United States Patent [19]

Ramsey, III

[11] 4,036,216

[45] July 19, 1977

[54] BODY FLUID PRESSURE SYSTEM

[76] Inventor: Maynard Ramsey, III, 2416 Watrous Ave., Tampa, Fla. 33609

[21] Appl. No.: 610,389

[22] Filed: Sept. 4, 1975

[51] Int. Cl.$^2$ .................................................. A61B 5/02
[52] U.S. Cl. ................................. 128/2.05 D; 73/395
[58] Field of Search ...................... 128/2.05 D, 2.05 E, 128/2.05 R, 2.05 A; 73/395, 402, 406, 407 R, 409

[56] References Cited

U.S. PATENT DOCUMENTS

| 2,877,799 | 3/1959 | Hildenbrandt, Jr. ................ 73/395 |
| 3,301,063 | 1/1967 | Kisling et al. ......................... 73/395 |
| 3,473,386 | 10/1969 | Nielsen, Jr. et al. ............ 128/2.05 D |
| 3,720,201 | 3/1973 | Ramsey ........................... 128/2.05 D |
| 3,865,100 | 2/1965 | Kanai et al. ..................... 128/2.05 D |

FOREIGN PATENT DOCUMENTS

| 577,283 | 5/1946 | United Kingdom ................... 73/395 |
| 1,197,796 | 7/1970 | United Kingdom ............ 128/2.05 A |

*Primary Examiner*—William E. Kamm

*Attorney, Agent, or Firm*—Gipple & Hale

[57] ABSTRACT

A disposable blood pressure monitor comprising an elongated tubular structure, adapted on one end to place its interior in direct communication with a fluid system to be monitored. A flexible tube shaped membrane is received within the tubular structure, separating the tubular structure into first and second chambers and a gauge assembly engages the other end of the tubular structure, to place the interior of the other chamber of the tubular structure in a pressure transfer communication with the fluid system to be monitored. The gauge assembly comprises a plug, a pressure measuring device mounted to the plug, a sensing tube extending through the plug and communicating with the pressure measuring device and a fluid filled sack member secured to the sensing tube. The sack member communicates with the pressure measuring device through the sensing tube and engages the inner wall of the flexible tube shaped membrane to place the gauge in a pressure responsive position with the fluid system to be monitored.

21 Claims, 5 Drawing Figures

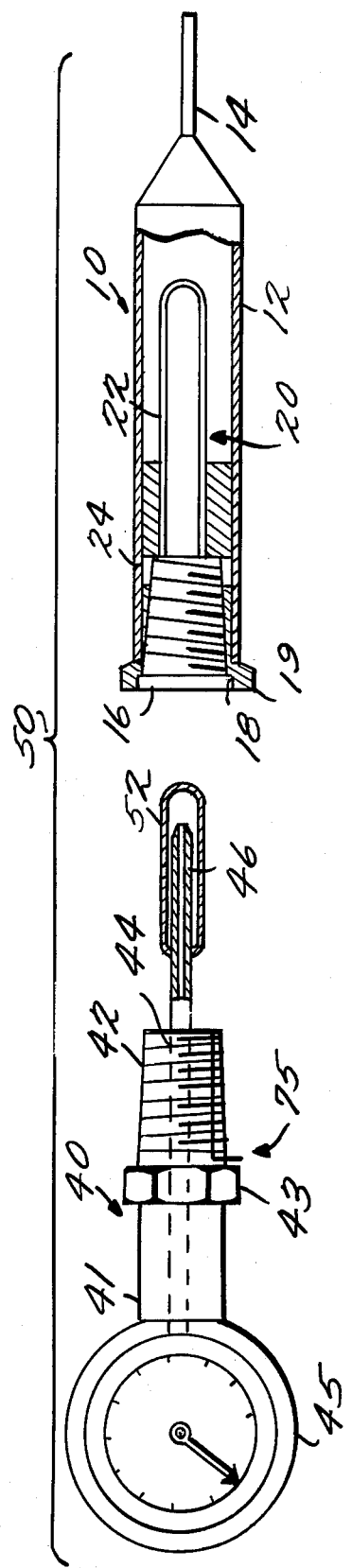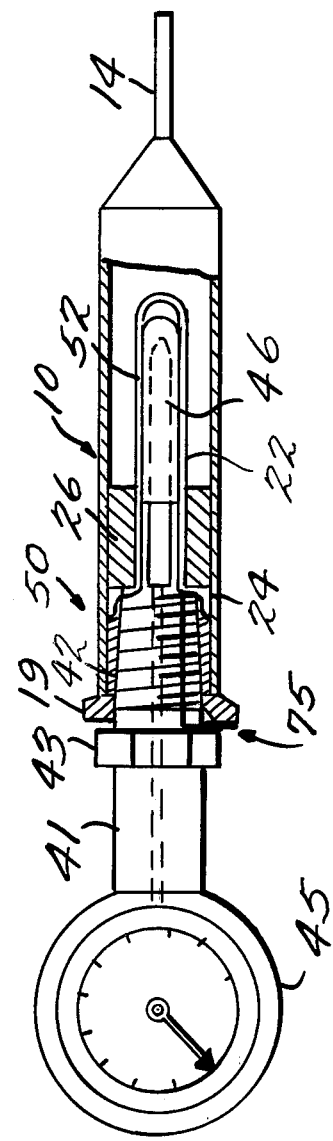

BODY FLUID PRESSURE SYSTEM

BACKGROUND OF THE INVENTION

The invention generally relates to pressure indicating devices of the type used for the measurement of body fluid pressures and more particularly to a direct reading, disposable manometer adapted for use in the measurement of arterial, venous blood and cerebrospinal fluid pressures.

FIELD OF THE INVENTION

The pressures of fluids in the vessels of all living things are indications of many facts which are of great value to those engaged in medical, biological and related fields. In the case of humans, the pressure in the vascular system is measured for many reasons, including diagnosis of pathology, laboratory routine for certain ailments, ascertainment of the progress of therapy, etc. As an example, the determination of venous blood pressure is in essential element in the diagnosis of a patient suspected of cargiac disease. Normal human venous blood pressure ranges between 80-120 millimeters water, whereas elevations of venous blood pressure above that range are found in cases of congestive heart failure.

Similarly, cerebrospinal fluid pressure normally ranges between 70-180 millimeters water, with elevated pressures being found, for example, in cases of intracranial tumor, supperative encephalitis, and cerbral abscess, hydatid cysts, extra, subdural, subarachnoid and intra cerebral hemorrhage, meningitis, acute encephalitis, hydrocephalus, craniostenosis, cerebral edema following head injury, acute nephritis, hypertensive encephalopathy and eclampsia. Lower than normal cerebrospinal pressures may be observed in such cases as spinal block by tumor, some subdural hematomas, and intracranial space occupying lesions which produce displacement of normal structures to cause pressure coning at the foramen magnum or tentorial opening.

The most common method of obtaining arterial blood pressure has been to gradually apply constrictive pressure about the limb of the patient until the flow of blood through a vessel has been arrested, as determined by listening to a stethoscope applied over the vessel at a point distal the point of constriction. Then, upon gradual release of the constricted pressure, the beginning of the flow through the vessel can be heard and the constricted pressure is noted on a gauge reading in millimeters of mercury. This pressure is referred to as systolic pressure. The pressure is then further gradually released until the sounds of the flow again cease and the pressure is again noted, which pressure is referred to as diastolic pressure. The difference between the diastolic pressure and systolic pressure is termed pulse pressure. Previous constriction pressure has been derived from an inflatable cuff connected to a mercury column manometer or to an aneroid type gauge having a dial scale calibrated in millimeters of mercury. While this common device is satisfactory for measuring the distolic-systolic pressure range for a discrete period of time, it has the obvious disadvantage of not being able to continuously monitor the patient's blood pressure.

DESCRIPTION OF THE PRIOR ART

In the prior art, many attempts have been made to devise blood pressure gauges which are portable, inexpensive and yet provide the attending physician with an accurate determination of the patient's blood pressure. One such device employs telescopically related, spring loaded tubes, the tubes being biased in an extended position. By exerting axial pressure on the tubes against an artery until the blood flow in that artery is cut off, and by monitoring the relative displacement of the tubes from the fully extended position required to produce such flow cut off, the systolic pressure is monitored. However, the means for monitoring the displacement of the tubes is often inconvenient of clumsy.

Another prior art device employs a pointer extending from an inner tube through a longitudinal slot in an outer tube, the outer tube having calibrated markings adjacent the slot. The disadvantage with this arrangement lies in the fact that the tubes, and hence the pointer, return to the original biased position upon removal of the instrument from the body, thereby requiring the operator to take a reading while exerting direct pressure. Such a technique has been found to be inconvenient.

Generally speaking, however, the indirect methods of making fluid pressure measurements, such as the ones described above, are not as accurate as any method which utilizes the particular fluid itself operating directly against a pressure sensing device.

Some direct intra-arterial pressure monitoring devices have been developed. One such device is shown in Surgery, Vol. 61, 1967, May, pp. 711-712, while another device is shown in Anesthesiology, Nov.-Dec. 1957, pp. 906-907.

In certain disposable manometers, such as those disclosed in U.S. Pat. Nos. 3,648,687 and 3,720,201 and 3,890,842, the lower plenum of the manometer tube as defined by a tube body and diaphram is filled with a non-compressible liquid. However, the upper plenum of the prior art apparatus is filled with air with the effect that the pressure transfer is dampened, so that only a mean pressure reading is obtainable.

SUMMARY OF THE INVENTION

The present invention comprises a disposable barrel assembly with a flexible diaphragm which divides the tube into upper and lower plena. The lower plenum can be filtered through the use of a novel disposable filling assembly which is disclosed in U.S. Pat. No. 3,890,842 or as shown in any of the previously identified prior art references so that a suitable incompressible fluid can be placed in the lower plenum of the tube for improved sensitivity to pressure differentials. The upper plenum of the barrel is adapted to receive a fluid filled pressure sensing sack attached to and communicating with a recording instrument such as a standard aneroid gauge or electronic pressure transducer and display device.

The complete device is designed to be sterilized and packaged at the point of manufacture with the barrel assembly being adapted to be thrown away after one use and another barrel assembly placed upon the gauge assembly for use.

The present invention overcomes the dampening effect through the use of the novel two stages construction which effectively permits essentially liquid to liquid contact, although thin flexible membranes actually separate the stages, thus allowing extremely accurate pressure reading. The two stages construction basically comprises a primary barrel assembly and a secondary gauge assembly. The insertion of the gauge assembly into the barrel assembly causes the diaphragm of the barrel assembly to be fully extended and directly contact the fluid portion of the gauge assembly so that pressure changes are readily transmitted. Thus, by eliminating any air in the system, the frequency response of the system is such that systolic and diastolic pressures can be readily determined.

It is thus seen that the present invention provides a disposable blood pressure manometer specifically adapted so that the barrel assembly can be disposed and the gauge assembly retained for additional usage.

A further object of the invention is to provide an apparatus for the measurement of fluid pressures in humans and animals which can be safely, quickly and easily used by laboratory technicians without any particular skill other than that provided by conventional training.

The present designed manometer is to simple and inexpensive in construction that the barrel assembly which is the only part of the apparatus that comes into contact with the patient can be discarded after use instead of having to be washed and resterilized, with the only sterilization being required at the place of manufacture where sterilization and adequate testing to assure sterility can be effect in mass production at little cost. Because of its simple construction, it can be filled with liquid and used safely, quickly and easily, in any physical environment.

The invention accordingly comprises the features of construction, combination of elements and arrangements of parts which will be exemplified in the construction hereinafter set forth and the scope of the invention will be indicated in the claims.

BRIEF DESCRIPTION OF THE DRAWINGS

FIG. 3 is a schematic cross sectional exploded view of the invention;

FIG. 4 is an assembled perspective view of the invention; and

Similar reference characters refer to similar parts throughout the several views of the drawings.

DETAILED DESCRIPTION OF THE PREFERRED EMBODIMENTS

Figure 1:
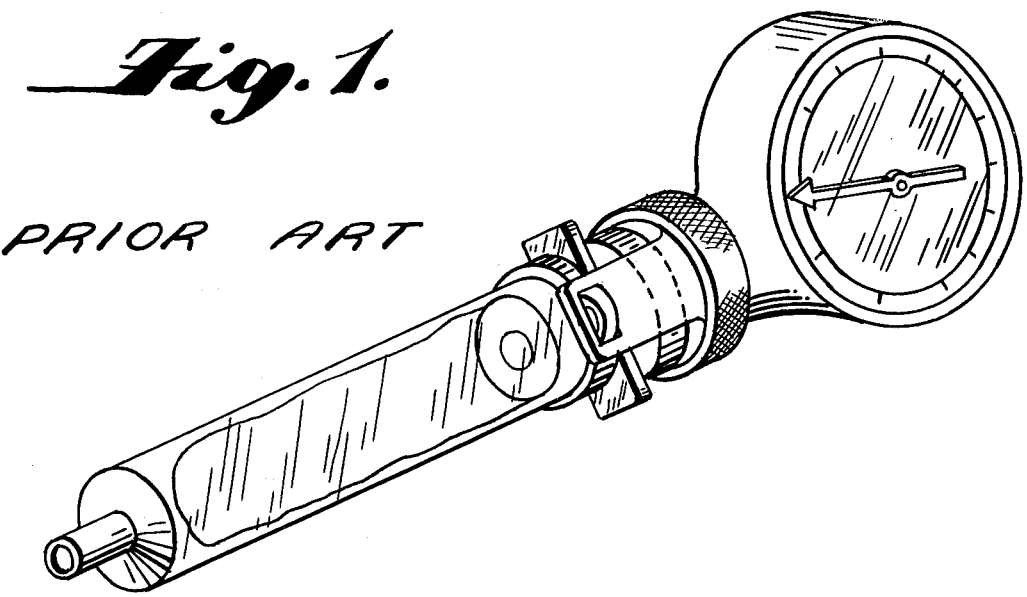
FIG. 1 is a perspective view of the prior art.

FIG. 1 shows a disposable body fluid pressure monitor as taught in U.S. Pat. No. 3,720,201.

Figure 2:
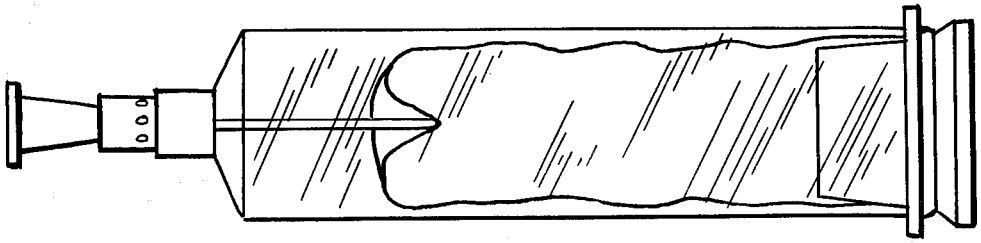
FIG. 2 is a side elevational view of another embodiment of the prior art.

FIG. 2 shows a body fluid pressure monitor as disclosed in U.S. Pat. No. 3,890,842.

Referring now to the drawings, 3–5 the assembled fluid contact disposable manometer of the present invention is shown and generally referred to by the reference number 50.

Manometer 50 comprises a barrel assembly 10 comprising a barrel or tube member 12 having at one end a catheter or hypodermic needle connector 14 and at the distal end a tube orifice 16 adapted to receive a gauge assembly 40. Inserted within barrel 12 is a flexible diaphragm 20 having a tubular saclike configuration which is placed in an airtight seal with the inner wall surface of the barrel 12, except for a small air passage 75 to allow escape of any air trapped between 52 and 20 when the two main structures are assembled together.

The orifice end 18 of the barrel is funnel shaped during manufacture so that the diameter of orifice 16 is wider than the barrel bore allowing it to receive the flexible diaphragm and gauge assembly. The end 18 is additionally provided with an outwardly extending flange 19 which aids in assembly and diassembly of the two manometer component assemblies.

The flexible diaphragm 20 is preferably constructed with a tubular sensing section 22 and anchor section 24 which is secured to the barrel inner wall surface below the funneled end by a non-toxic adhesive. If desired a doughnut shaped positioning member 26 can be used to position the tubular sensing section 22 within the bore of the barrel. The doughnut member 26 has an orifice of sufficient diameter to allow tube section 22 to pass through it and an outer body diameter equal to or smaller than the diameter of the bore of the barrel 12. Once the flexible diaphragm 20 has been secured in the barrel 12, a non-compressible fluid can be received in the barrel through connector 14 convering the outer surface of the tube section 22. Each time that barrel assembly 10 is used it can be removed from the gauge assembly 40, disposed of and replaced with a new barrel assembly 10.

The distal end 18 of the barrel can be threaded to receive a threaded plug 42 of the integral gauge assembly 40.

The gauge assembly 40 comprises a housing 41 having a threaded plug 42 and an integral stop member 43 in the form of a nut allowing the gauge assembly to be easily screwed down into the flexible diaphragm 20. An aneroid gauge 45 is mounted on the housing. The plug 42 is of a frustro conical construction with a tapering outer surface thereby providing a tighter fit in the funnel shaped end of barrel 12. A through going bore 44 is provided through plug 42 and nut 43 into which a hollow sensing stem 46 of the aneroid gauge is inserted. The plug 42 can alternately be formed with thread-cutting threads so that threads are formed in the plug receiving end 18 as the plug is screwed into the barrel. A flexible enclosed blunt ended sensing member 52 is secured to the stem to form a fluid tight assembly. The sensing member 52 comprises a flexible sack member membrane surrounding the top of the sensing stem filled with a non-compressible liquid. The sack member has a diameter slightly smaller than the bore of the tubular section 22 so that the sensing stem 46 and associated sack member 52 can be inserted into the bore of the tubular shaped flexible diaphragm 20 thus allowing essentially fluid to fluid surface contact as the flexible membrane and sack member are actually in contact. As previously mentioned the size and shape of the flexible sack member 52 on the gauge stem 46 is similar to the tubular membrane section 22 in the disposable barrel assembly, except of course, that its diameter is preferably slightly smaller, allowing air to leak out of the thin area defined between the two membranes when the two devices are assembled together. The pressure from fluid originating from the patient into the distal end of the disposable monitor device compresses the membrane section 22 against the sack member membrane 52, thus eliminating all air from the system. Since all air is eliminated from the system, the frequency response will be increased and allow systolic and diastolic pressures to be measured.

Figure 5:
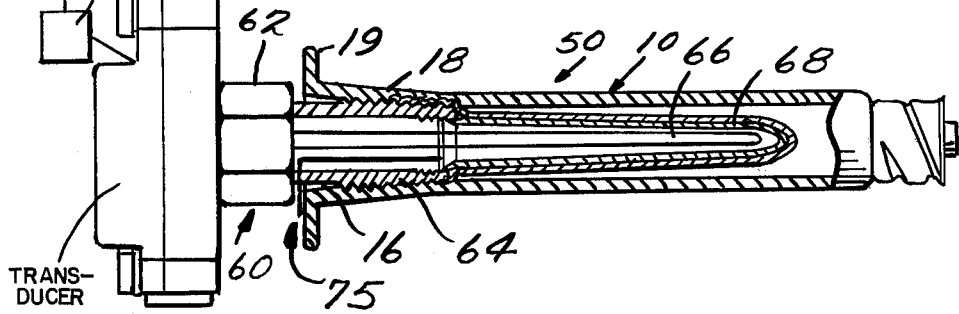
FIG. 5 is another embodiment of the invention partially in section with a transducer attachment.

As shown in FIG. 5 the gauge assembly is in the form of a transducer 54 rather than the aneroid gauge 45 shown in FIGS. 3 and 4. The transducer 54 is connected by circuitry 56 schematically shown and known in the art to a digital readout device 58 so that the electrical signals generated by the transducer by the blood pressure of the system are converted into digital or analog display. In FIG. 5 the transducer 54 is mounted to a housing 60 defining a stop nut 62 and a tapered plug 64. A sensing stem 66 extends from the transducer through a bore cut in the nut and integrally tapered plug. The extending portion of the stem is covered by a fluid filled sack member 68 which is shown as being mounted to the transducer housing. However the sack can be secured to the sensing stem 66 or the transducer itself.

In another embodiment not shown, the fluid filled sack 52, 68 of the gauge is initially empty and is filled by a fluid filled needle that would be inserted into the gauge stem thus making fluid continuity between the disposable component and the pressure sensing component. It is apparent from the conclusions of the invention that the sensing device could be a fluid filled gauge transducer or any other suitable sensing unit.

The various elements of the disposable manometer may be of any suitable lightweight substance such as plastic which will facilitate easy handling and use.

It will thus be seen that the objects set forth above and those made apparent from the preceding detailed description are efficiently attained and since certain changes may be made in the above construction without departing from the scope of the invention, it is intended that all matter contained in the above-detailed description or shown in the accompanying drawings, shall be interpreted as illustrative and not as a limitation.

What is claimed is:

1. A disposable blood pressure monitor comprising an elongated tubular structure, means on one end of said tubular structure adapted to place the interior of said tubular structure in direct communication with a fluid system to be monitored, a flexible tube shaped membrane received within said tubular structure, said flexible tube shaped membrane separating said tubular structure into first and second chambers, gauge means engaging the other end of said tubular structure, said gauge means being removably in said tubular structure and adapted to place the interior of said tubular structure in a pressure transfer communication with the fluid system to be monitored, said gauge means comprising a plug means, a pressure indicating means mounted to said plug means, a tube means extending through said plug means and communicating with said pressure indicating means, sensor means mounted on said tube means and an incompressible fluid filled sack member secured to said tube means and containing said sensor means, said sack member communicating with said pressure indicating means, and engaging the inner wall of said flexible tube shaped membrane through said tube means placing said gauge means in a pressure responsive communication with the fluid system to be monitored.

2. A disposable blood pressure monitor as claimed in claim 1 wherein said tube means comprises a tube member defining a bore secured to said gauge means to allow communication of said gauge with said sack member.

3. A disposable blood pressure monitor as claimed in claim 1 wherein said sack member has a blunt end having the same configuration as an end of the flexible tube shaped membrane.

4. A disposable blood pressure monitor as claimed in claim 2 wherein said sack member is tubular shaped and has a smaller diameter than the inner bore diameter of said flexible tube shaped membrane.

5. A disposable blood pressure monitor as claimed in claim 2 wherein said gauge means includes a threaded plug means, said threaded plug means being adapted to engage the interior of said flexible tube shaped membrane to form a fluid tight seal.

6. A disposable blood pressure monitor as claimed in claim 1 wherein said pressure indicating means comprises a transducer connected by circuit means to a visual readout device.

7. A disposable blood pressure monitor as claimed in claim 1 wherein said pressure indicating means is an aneroid gauge.

8. A disposable blood pressure monitor as claimed in claim 1 wherein said gauge means includes a plug member provided with thread cutting threads.

9. A disposable blood pressure monitor as claimed in claim 1 wherein said tubular structure defines a flange on one end of said gauge means has a stop secured thereto adapted to abut said flanged end to limit the distance that the gauge means can be inserted into the tubular structure.

10. A disposable blood pressure monitor as claimed in claim 1 wherein a ring shaped member is positioned around said flexible tube shaped member to place said tube shaped membrane in a predetermined position inside said elongated tubular structure, 11. A disposable blood pressure monitor with a reuseable assembly using a transducer for measuring the blood pressure in a system comprising an elongated tubular structure, connector means formed on one end of said tubular structure adapted to place the interior of said tubular structure in direct communication with a fluid system to be monitored, a flexible saclike membrane positioned within said tubular structure to separate said tubular structure into first and second chambers, said reuseable assembly being mounted to the other end of said tubular structure, said reuseable assembly comprising transducer means including a plug means removably mounted to and sealing the other end of said tubular structure, said transducer means comprising a transducer housing, a transducer assembly mounted within said housing, a tubular sack member filled with an incompressible liquid mounted to said housing, a sensor means connected to said transducer assembly and extending outside of said housing and contained within said tubular sack member giving said sack member semirigid form allowing it to be inserted inside said flexible saclike membrane.

12. A disposable blood pressure monitor as claimed in claim 11 including circuit means connected to said transducer assembly and pressure indicating means connected to said circuit means, said circuit means transmitting electrical equivalents of pressure variations occurring in said tubular structure in the form of electrical signals to said indicating means which registers said signals in a readable form.

13. A disposable blood pressure monitor as claimed in claim 12 wherein said pressure indicating means is a digital readout apparatus.

14. A disposable blood pressure monitor as claimed in claim 11 wherein the outer diameter of said transducer sac member is smaller than the diameter of the bore of the saclike flexible membrane.

15. A disposable blood pressure monitor as claimed in claim 11 wherein said other end of said tubular structure is inclined outwardly from the body of said tubular structure and has an outwardly extending flange.

16. A disposable blood pressure monitor comprising a disposable assembly and a reuseable assembly, said disposable assembly comprising an elongated tubular structure, means on one end of said tubular structure adapted to place the interior of said tubular structure in direct communication with a fluid system to monitor, a flexible tube shaped membrane received within said tubular structure, said flexible tube shaped membrane separating said tubular structure into first and second chambers, said reuseable assembly comprising gauge means removably engaging the other end of said tubular structure, said gauge means comprising a housing defining a plug adapted to engage the other end of said tubular structure, said plug being provided with a fluid passage means, a pressure indicating means mounted to said housing, a sensing stem connected to said pressure indicating means and extending through said plug, and a sack member filled with an incompressible liquid secured to one end of said sensing stem, said sack member having a smaller diameter than the inner diameter of said flexible tube shaped membrane allowing it to be inserted therein so that when the interior of said tube structure comes in direct communication with the fluid system to be monitored the pressure from the fluid compresses the flexible tube shaped membrane against the fluid filled sack member forcing all of the air through said fluid passage means from the flexible tube shaped membrane allowing said pressure indicating means to be in communication with the fluid system being monitored.

17. A disposable blood pressure monitor as claimed in claim 16 wherein said pressure indicating means is an aneroid gauge.

18. A disposable blood pressure monitor as claimed in claim 16 wherein said pressure indicating means comprises a transducer assembly connected by circuit means to a visual readout device.

19. A disposable blood pressure monitor comprising an elongaged tubular structure, means on one end of said tubular structure adapted to place the interior of said tubular structure in direct communication with a fluid system to be monitored, a thin flexible tube shaped membrane received within said tubular structure, said thin flexible tube shaped membrane separating said tubular structure into first and second chambers, removable and reuseable gauge means engaging the other end of said tubular structure, said gauge means comprising a housing defining a plug adapted to engage the other end of said tubular structure, a pressure indicating means mounted to said housing, a sensing means connected to said pressure indicating means and extending through and from said plug, a sack member filled with an incompressible fluid secured to said housing and surrounding an extended portion of said sensing means, said sack member having a smaller diameter than the inner diameter of said flexible tube shaped membrane so that when said plug engages the other end of said tubular structure the fluid filled sack member is inserted into the flexible tube shaped membrane with the result that when the interior of said tubular structure comes in direct communication with the fluid system to be monitored, the pressure from the fluid compresses the flexible tube shaped membrane against the fluid filled sack member forcing all of the air from the flexible tube shaped membrane allowing said pressure indicating means to be in substantially fluid to fluid communication with the fluid system being monitored.

20. A disposable blood pressure monitor as claimed in claim 19 wherein said pressure indicating means is an aneroid gauge.

21. A disposable blood pressure monitor as claimed in claim 19 wherein said pressure indicating means is a transducer assembly connected by circuit means to a visual readout device.

* * * * *